United States Patent
Kim et al.

(10) Patent No.: US 8,993,272 B2
(45) Date of Patent: Mar. 31, 2015

(54) **MICROORGANISMS OF *CORYNEBACTERIUM* WITH IMPROVED 5'-INOSINIC ACID PRODUCTIVITY, AND METHOD FOR PRODUCING NUCLEIC ACIDS USING SAME**

(75) Inventors: Jeong Hwan Kim, Seoul (KR); Jung Gun Kwon, Seoul (KR); Tae Min Ahn, Gyeonggi-Do (KR); Soo Youn Hwang, Yongin-si (KR); Min Ji Baek, Seoul (KR); Na Ra Kwon, Seoul (KR); Nan Young Yoon, Seoul (KR); Ju Jeong Kim, Suwon-si (KR)

(73) Assignee: CJ Cheiljedang Corporation, Seoul (KR)

( * ) Notice: Subject to any disclaimer, the term of this patent is extended or adjusted under 35 U.S.C. 154(b) by 0 days.

(21) Appl. No.: 13/262,202
(22) PCT Filed: Mar. 23, 2010
(86) PCT No.: PCT/KR2010/001760
§ 371 (c)(1), (2), (4) Date: Sep. 29, 2011
(87) PCT Pub. No.: WO2010/114245
PCT Pub. Date: Oct. 7, 2010

(65) Prior Publication Data
US 2012/0021466 A1    Jan. 26, 2012

(30) Foreign Application Priority Data
Apr. 1, 2009 (KR) .................. 10-2009-0028145

(51) Int. Cl.
*C12P 19/32* (2006.01)
*C12N 1/20* (2006.01)
(Continued)

(52) U.S. Cl.
CPC .............. *C12P 19/34* (2013.01); *C12N 9/1235* (2013.01); *C12P 19/32* (2013.01); *C12R 1/15* (2013.01)

USPC ............ 435/92; 435/243; 435/252.1; 435/41; 435/170

(58) Field of Classification Search
None
See application file for complete search history.

(56) References Cited

U.S. PATENT DOCUMENTS 6,586,214 B1    7/2003  Duncan et al.
7,244,608 B2 *  7/2007  Kim et al. ................. 435/252.3
(Continued)

FOREIGN PATENT DOCUMENTS

EP    1004663 A1    5/2000
EP    2011860 A1    1/2009
(Continued)

OTHER PUBLICATIONS

Tomita et al., "Stimulation by L Proline of 5' Inosinic Acid Production by Mutants of *Corynebacterium-ammoniagenes*," Agricultural and Biological Chemistry, Japan Soc. for Bioscience, Biotechnology and Agrochem., Jan. 1, 1991, pp. 2221-2226, vol. 55, No. 9.
(Continued)

*Primary Examiner* — Blaine Lankford
*Assistant Examiner* — Thomas J Visone
(74) *Attorney, Agent, or Firm* — Joseph R. Baker, Jr.; Gavrilovich, Dodd & Lindsey LLP

(57) ABSTRACT

The present invention relates to a microorganisms of the genus *Corynebacterium* producing 5'-inosinic acid, in which the expression of genes encoding purine biosynthesis related enzymes is increased higher than the intrinsic expression, and to a method for producing 5'-inosinic acid, comprising culturing the microorganisms of the genus *Corynebacterium* with improved 5'-inosinic acid productivity.

2 Claims, 7 Drawing Sheets

(51) Int. Cl.
*C12P 19/34* (2006.01)
*C12N 9/12* (2006.01)
*C12R 1/15* (2006.01)

(56) References Cited

U.S. PATENT DOCUMENTS 7,435,560 B1 * 10/2008 Matsui et al. .................. 435/87
2010/0143984 A1 * 6/2010 Park et al. .................... 435/115

FOREIGN PATENT DOCUMENTS

| JP | 63-248394 | | 10/1998 | |
|---|---|---|---|---|
| KR | 2003-0042972 | A | 6/2003 | |
| KR | 10-2006-0098340 | A | 9/2006 | |
| KR | 10-20060098340 | A | 9/2006 | |
| KR | 10-0785248 | B1 | 12/2007 | |
| KR | 10-20080025355 | A | 3/2008 | |
| KR | 10-0857379 | B1 | 9/2008 | |
| WO | 2007125782 | A1 | 11/2007 | |
| WO | WO 2008/033001 | * | 3/2008 | C12N 1/21 |
| WO | 2008-088156 | A1 | 7/2008 | |

OTHER PUBLICATIONS

Roscoe, Richard, Extended European Search Report, EP 10 75 8970, European Patent Office, Aug. 13, 2012.

Ishii, Kenji and Shiio, Isamu, "Improved Inosine Production and Derepression of Purine Nucleotide Biosynthetic Enzymes in 8-Azaguanine Resistant Mutants of *Bacillus subtilis*", Agr. Biol. Chem., 1972, vol. 36, No. 9, pp. 1511-1522.

Shimaoka, Megumi et al., "Effect of Amplification of Desensitized purF and prs on Inosine Accumulation in *Escherichia coli*", Journal of Bioscience and Bioengineering, 2007, vol. 103, No. 3, pp. 255-261.

Shimaoka et al., "Effect of Amplification of Desensitized purF and prs on Inosine Accumulation in *Escherichi coli*," J. of Bioscience and Bioengineering, 2007, pp. 255-261, vol. 103, No. 3.

Korean Intellectual Property Office, International Search Report, PCT/KR2010/001760, Apr. 29, 2011.

Collins, M.D., "Transfer of Brevibacterium ammoniagenese (Cooke and Keith) to the Genus *Corynebacterium* as *Corynebacterium ammoniagenes* comb. nov.", International Journal of Systematic Bacteriology, 1987, vol. 1. 37, No. 4, pp. 442-443.

Hayashi, Mikiro et al., "Transcriptorne Analysis of Acetate Metabolism in *Corynebacterium glutamicum* Using a Newly Developed Metabolic Array", Biosci. Biotechnol. Biochem., 66 (6), 1337-1344, 2002.

Yoshida, Tomomi, Japanese Patent Application No. 2012-503311, Japanese Patent Office, Oct. 1, 2013.

* cited by examiner

US 8,993,272 B2

MICROORGANISMS OF CORYNEBACTERIUM WITH IMPROVED 5'-INOSINIC ACID PRODUCTIVITY, AND METHOD FOR PRODUCING NUCLEIC ACIDS USING SAME

CROSS REFERENCE TO RELATED APPLICATIONS

This application is a U.S. National Stage Application filed under 35 U.S.C. §371 and claims priority to International Application No. PCT/KR2010/001760, filed Mar. 23, 2010, which application claims priority to Korean Application No. 10-2009-0028145, filed Apr. 1, 2009, the disclosure of which are incorporated herein by reference in their entirety.

BACKGROUND OF THE INVENTION

1. Field of the Invention

The present invention relates to a microorganism belonging to the genus *Corynebacterium* producing 5'-inosinic acid, in which the expression of genes encoding purine biosynthesis related enzymes is increased higher than the intrinsic expression, and a method for producing 5'-inosinic acid, comprising culturing the microorganism of the genus *Corynebacterium* with improved 5'-inosinic acid productivity.

DEPOSIT OF MICROORGANISM

Exemplary microorganisms of the disclosure were deposited on Nov. 16, 2004 with the Korean Culture Center of Microorganisms having an address of 361-221, Yurim B/D, Hongje-1-dong, Seodaemun-gu, Seoul, 120-091, Republic of Korea, as Accession Number KCCM-10610 (designation *Corynebacterium ammoniagenes* CJIP2401) under the Budapest Treaty. This deposit will be maintained at an authorized depository and replaced in the event of mutation, non-viability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

Exemplary microorganisms of the disclosure were deposited on Feb. 19, 2009 with the Korean Culture Center of Microorganisms having an address of 361-221, Yurim B/D, Hongje-1-dong, Seodaemun-gu, Seoul, 120-091, Republic of Korea, as Accession Number KCCM-10992P (designation *Corynebacterium ammoniagenes* CNO1-0316) under the Budapest Treaty. This deposit will be maintained at an authorized depository and replaced in the event of mutation, non-viability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the application.

2. Description of the Related Art

One of the nucleotide compounds, 5'-inosinic acid is an intermediate material of the metabolic system of nucleotide biosynthesis, which is used in a variety of fields such as foods, medicines, and other various medical areas and functions to play an important role in animal and plant physiology. In particular, 5'-inosinic acid is a nucleotide seasoning, which has drawn much attention as a savory seasoning, because it has synergistic effects when used with monosodium glutamate (MSG).

So far well known processes for producing 5'-inosinic acid include a process of enzymatically decomposing ribonucleic acid extracted from yeast cells (Japanese Published Examined Patent Application No. 1614/1957, etc), a process of chemically phosphorylating inosine produced by fermentation (Agric. Biol. Chem., 36, 1511 (1972), etc) and a process of culturing a microorganism capable of producing 5'-inosinic acid and recovering inosine monophosphate (IMP) accumulated in the medium. Currently, the processes of producing 5'-inosinic acid using microorganisms are mostly used. The strains of the genus *Corynebacterium* are widely used as a microorganism for the production of 5'-inosinic acid, and for example, a method for producing 5'-inosinic acid by culturing *Corynebacterium ammoniagenes* is disclosed (Korean Patent Publication No. 2003-0042972).

To improve a production yield of 5'-inosinic acid by a microorganism, studies have been made to develop strains by increasing or decreasing activity or expression of the enzymes involved in the biosynthetic or degradative pathway of 5'-inosinic acid. Korean Patent No. 785248 discloses a microorganism in which a purC gene encoding phosphoribosylaminoimidazole succinocarboxamide synthetase is overexpressed in the purine biosynthetic pathway and a method for producing 5'-inosinic acid using the same. In addition, Korean Patent No. 857379 discloses a *Corynebacterium ammoniagenes* strain in which the purKE—encoded phosphoribosylaminoimidazole carboxylase is overexpressed and a method for producing high concentration of IMP in a high yield using the same.

However, there is still a need to develop a strain capable of producing 5'-inosinic acid in a higher yield and a method for producing 5'-inosinic acid using the same.

Therefore, the present inventors have conducted studies to develop a strain capable of producing 5'-inosinic acid with high productivity. As a result, they found that the productivity of 5'-inosinic acid can be improved by simultaneously increasing activities of the major enzymes involved in the purine biosynthesis pathway higher than the intrinsic activity, thereby completing the present invention.

SUMMARY OF THE INVENTION

An object of the present invention is to provide a microorganism of the genus *Corynebacterium* having improved 5'-inosinic acid productivity.

Another object of the present invention is to provide a method for producing 5'-inosinic acid using the microorganism of the genus *Corynebacterium* having improved 5'-inosinic acid productivity.

DETAILED DESCRIPTION OF THE PREFERRED EMBODIMENTS

Figure 1:
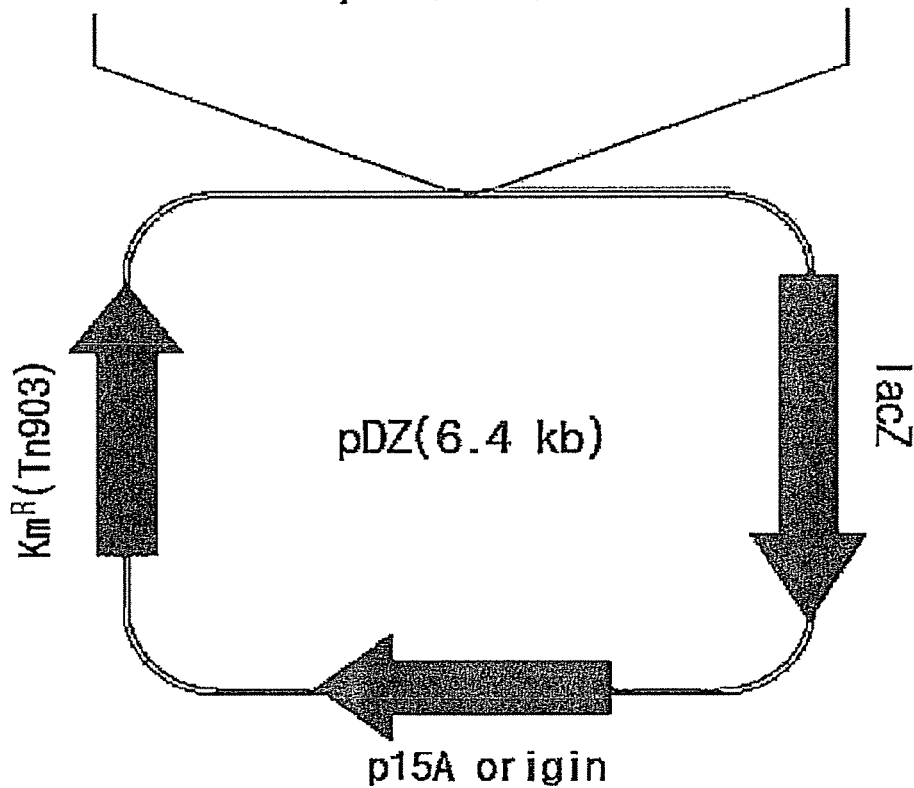
FIG. 1 shows a pDZ vector for chromosomal insertion into the microorganism of the genus *Corynebacterium*.

In order to achieve the above objects, the present invention provides a microorganism belonging to the genus *Corynebacterium* producing 5'-inosinic acid, in which the expression of genes encoding purine biosynthesis related enzymes is increased higher than the intrinsic expression.

The microorganism of the genus *Corynebacterium* of the present invention has more improved 5'-inosinic acid productivity than a parental strain, because the expression of genes encoding purine biosynthesis related enzymes is increased higher than the intrinsic expression.

As used herein, the term "purine biosynthesis related enzyme" means an enzyme that catalyzes the reaction involved in the purine biosynthesis pathway producing a purine base as a final product, and includes phosphoribosylpyrophosphate amidotransferase, phosphoribosylglycinamide formyltransferase, phosphoribosylformylglycinamidin synthetase, phosphoribosylformylglycinamidin synthetase phosphoribosylaminoimidazole synthetase, phosphoribosylaminoimidazole carboxylase, phosphoribosyl aminoimidazole succinocarboxamide synthetase, inosinic acid cyclohydrolase, ribosephosphate pyrophosphokinase or the like.

In a specific embodiment of the present invention, the purine biosynthesis related enzymes may be a combination of one or more enzymes selected from the group consisting of phosphoribosylpyrophosphate amidotransferase, phosphoribosylglycinamide formyltransferase, phosphoribosylformylglycinamidin synthetase, phosphoribosylformylglycinamidin synthetase phosphoribosylaminoimidazole synthetase, phosphoribosylaminoimidazole carboxylase, phosphoribosyl aminoimidazole succinocarboxamide synthetase and inosinic acid cyclohydrolase, and ribosephosphate pyrophosphokinase.

In a specific embodiment of the present invention, the gene encoding purine biosynthesis related enzymes, of which expression is increased higher than the intrinsic expression, are a combination of a purN gene of SEQ ID NO. 36, which codes for phosphoribosylglycinamide formyltransferase, a purS gene of SEQ ID NO. 37, which codes for phosphoribosylformylglycinamidin synthetase, a purL gene of SEQ ID NO. 38, which codes for phosphoribosylformylglycinamidin synthetase II, a purKE gene of SEQ ID NO. 40, which codes for phosphoribosylaminoimidazole carboxylase, a purC of SEQ ID NO. 41, which codes for phosphoribosyl aminoimidazole succinocarboxamide synthetase, a purH gene of SEQ ID NO. 42, which codes for inosinic acid cyclohydrolase, and a prs gene of SEQ ID NO. 43, which codes for ribosephosphate pyrophosphokinase.

In a specific embodiment of the present invention, the gene encoding purine biosynthesis related enzymes, of which expression is increased higher than the intrinsic expression, are a combination of a purF gene of SEQ ID NO. 35, which codes for phosphoribosylpyrophosphate amidotransferase, a purN gene of SEQ ID NO. 36, which codes for phosphoribosylglycinamide formyltransferase, a purS gene of SEQ ID NO. 37, which codes for phosphoribosylformylglycinamidin synthetase, a purL gene of SEQ ID NO. 38, which codes for phosphoribosylformylglycinamidin synthetase II, a purM gene of SEQ ID NO. 39, which codes for phosphoribosylaminoimidazole synthetase, a purKE gene of SEQ ID NO. 40, which codes for phosphoribosylaminoimidazole carboxylase, a purC of SEQ ID NO. 41, which codes for phosphoribosyl aminoimidazole succinocarboxamide synthetase, a purH gene of SEQ ID NO. 42, which codes for inosinic acid cyclohydrolase, and a prs gene of SEQ ID NO. 43, which codes for ribosephosphate pyrophosphokinase.

As used herein, the term "increased higher than the intrinsic expression" means that the gene expression level is higher than that in naturally expressed in a microorganism or higher than that expressed in a parental strain, and includes an increase in the number (copy number) of the genes encoding corresponding enzyme and the expression level increased thereby or an increase in the expression level by mutation or an increase in the expression level by both of them.

In a specific embodiment of the present invention, the increase in the expression level of the gene encoding purine biosynthesis related enzyme includes the increase in the copy number of the gene by additionally introducing the corresponding foreign gene into a strain or by amplifying the intrinsic gene, or the increase in transcription efficiency or translation efficiency by mutation in the transcription or translation regulatory sequence, but is not limited thereto. The amplification of the intrinsic gene may be easily performed by a method known in the art, for example, by cultivation under a suitable selection pressure.

In a specific embodiment of the present invention, the expression level of the gene encoding purine biosynthesis related enzyme may be increased by additionally introducing the gene encoding purine biosynthesis related enzyme into a cell or by amplifying the intrinsic gene encoding the purine biosynthesis related enzyme.

In a specific embodiment of the present invention, the gene encoding purine biosynthesis related enzyme, of which the expression level is increased higher than the intrinsic expression, may exist as two or more copies in the microorganism of the genus *Corynebacterium* having improved 5'-inosinic acid productivity by introducing one or more copies into a cell, in addition to the corresponding intrinsic gene.

In a specific embodiment of the present invention, the gene encoding purine biosynthesis related enzyme is introduced into the microorganism of the genus *Corynebacterium* having improved 5'-inosinic acid productivity by transformation using a recombinant vector containing two copies of the corresponding gene that are consecutively arranged.

In a specific embodiment of the present invention, the recombinant vector used for preparation of the microorganism of the genus *Corynebacterium* having improved 5'-inosinic acid productivity may be selected from the group consisting of pDZ-2purFM, pDZ-2purNH, pDZ-2purSL, pDZ-2purKE, pDZ-2purC, and pDZ-2prs recombinant vectors, which have the cleavage maps of FIGS. 2 to 7 respectively, depending on the genes introduced.

In a specific embodiment of the present invention, the microorganism of the genus *Corynebacterium* having improved 5'-inosinic acid productivity may be derived from *Corynebacterium* microorganisms capable of producing 5'-inosinic acid. For example, the microorganism of the genus *Corynebacterium* having improved 5'-inosinic acid productivity according to the present invention may be derived from *Corynebacterium ammoniagenes* ATCC6872, *Corynebacterium thermoaminogenes* FERM BP-1539, *Corynebacterium glutamicum* ATCC13032, *Brevibacterium flavum*

ATCC14067, *Brevibacterium lactofermentum* ATCC13869, and strains prepared therefrom.

In a specific embodiment of the present invention, the microorganism of the genus *Corynebacterium* having improved 5'-inosinic acid productivity may include two or more copies of the gene encoding purine biosynthesis related enzyme.

In a specific embodiment of the present invention, the microorganism of the genus *Corynebacterium* having improved 5'-inosinic acid productivity may be *Corynebacterium* ammonia genes, and more preferably a transformed *Corynebacterium ammoniagenes*, in which the activity of a combination of the prs gene and one or more genes selected from the group consisting of purF, purN, purS, purL, purM, purKE, purC, and purH is increased to produce high concentration of 5'-inosinic acid.

In a specific embodiment of the present invention, the microorganism of the genus *Corynebacterium* having improved 5'-inosinic acid productivity may be a strain, in which the 5'-inosinic acid-producing *Corynebacterium ammoniagenes* CJIP2401 (KCCM-10610) strain is introduced with each of the pDZ-2purFM, pDZ-2purNH, pDZ-2purSL, pDZ-2purKE, pDZ-2purC, and pDZ-2prs recombinant vectors having the cleavage maps of FIGS. 2, 3, 4, 5, 6, and 7 in order or in combination, and one of two copies of the introduced purF, purN, purS, purL, purM, purKE, purC, purH and prs genes are substituted for the corresponding intrinsic genes by homologous recombination, and thus each two copies of the purF, purN, purS, purL, purM, purKE, purC, purH, and prs genes are inserted into the strain.

In a specific embodiment of the present invention, the microorganism of the genus *Corynebacterium* having improved 5'-inosinic acid productivity may be *Corynebacterium* ammonia genes containing two copies of the genes encoding purine biosynthesis related enzymes that are a combination of the purN gene of SEQ ID NO. 36, which codes for phosphoribosylglycinamide formyltransferase, the purS gene of SEQ ID NO. 37, which codes for phosphoribosylformylglycinamidin synthetase, the purL gene of SEQ ID NO. 38, which codes for phosphoribosylformylglycinamidin synthetase II, the purKE gene of SEQ ID NO. 40, which codes for phosphoribosylaminoimidazole carboxylase, the purC of SEQ ID NO. 41, which codes for phosphoribosyl aminoimidazole succinocarboxamide synthetase, the purH gene of SEQ ID NO. 42, which codes for inosinic acid cyclohydrolase, and the prs gene of SEQ ID NO. 43, which codes for ribosephosphate pyrophosphokinase, and preferably *Corynebacterium ammoniagenes* CN01-0120.

In a specific embodiment of the present invention, the microorganism of the genus *Corynebacterium* having improved 5'-inosinic acid productivity may be *Corynebacterium ammoniagenes* containing two copies of the genes encoding purine biosynthesis related enzymes that are a combination of the purF of SEQ ID NO. 35, which codes for phosphoribosylpyrophosphate amidotransferase, the purN gene of SEQ ID NO. 36, which codes for phosphoribosylglycinamide formyltransferase, the purS gene of SEQ ID NO. 37, which codes for phosphoribosylformyiglycinamidin synthetase, the purL gene of SEQ ID NO. 38, which codes for phosphoribosylformylglycinamidin synthetase II, the purM of SEQ ID NO. 39, which codes for phosphoribosylaminoimidazole synthetase, the purKE gene of SEQ ID NO. 40, which codes for phosphoribosylaminoimidazole carboxylase, the purC of SEQ ID NO. 41, which codes for phosphoribosyl aminoimidazole succinocarboxamide synthetase, the purH gene of SEQ ID NO. 42, which codes for inosinic acid cyclohydrolase, and the prs gene of SEQ ID NO. 43, which codes for ribosephosphate pyrophosphokinase, and preferably *Corynebacterium ammoniagenes* CN01-0316 (KCCM 10992P).

Further, the present invention provides a method for producing 5'-inosinic acid, comprising the steps of culturing the microorganism belonging to the genus *Corynebacterium* producing 5'-inosinic acid, in which the expression of a gene encoding purine biosynthesis related enzyme is increased higher than the intrinsic expression, and recovering 5'-inosinic acid from the culture medium.

In the method for producing 5'-inosinic acid of the present invention, the medium and other culture conditions used for the cultivation of the microorganism of the genus *Corynebacterium* may be the same as those typically used in the cultivation of the microorganism of the genus *Corynebacterium*, and easily selected and adjusted by those skilled in the art. In addition, the cultivation may be performed by any cultivation method known to those skilled in the art, for example, batch, continuous, and fed-batch culture, but is not limited thereto.

In a specific embodiment of the present invention, the microorganism belonging to the genus *Corynebacterium* producing 5'-inosinic acid may be *Corynebacterium ammoniagenes*.

In a specific embodiment of the present invention, the microorganism belonging to the genus *Corynebacterium* producing 5'-inosinic acid may be *Corynebacterium ammoniagenes* CN01-0120 or *Corynebacterium ammoniagenes* CNO1-0316 (KCCM 10992P).

In a specific embodiment of the present invention, culturing the microorganism of the genus *Corynebacterium* is performed by culturing the strain in a conventional medium containing suitable carbon sources, nitrogen sources, amino acids, vitamins or the like under aerobic conditions by adjusting temperature, pH or the like.

As a carbon source, carbohydrates such as glucose and fructose may be used. As a nitrogen source, various inorganic nitrogen sources such as ammonia, ammonium chloride, and ammonium sulphate may be used, and organic nitrogen sources such as peptone, NZ-amine, beef extract, yeast extract, corn steep liquor, casein hydrolysate, fish or fish meal, and defatted soybean cake or meal may be used. Examples of the inorganic compounds include potassium monohydrogen phosphate, potassium dihydrogen phosphate, magnesium sulfate, ferrous sulfate, manganese sulfate, and calcium carbonate. When needed, vitamins and auxotrophic bases may be used.

The cultivation is performed under aerobic conditions, for example, by shaking culture or stirring culture, preferably at a temperature of 28 to 36° C. During the cultivation, the pH is preferably maintained within the range of pH 6 to 8. The cultivation may be performed for 4 to 6 days.

Hereinafter, the present invention will be described in more detail with reference Examples. However, these Examples are for illustrative purposes only, and the invention is not intended to be limited by these Examples.

EXAMPLE 1

Insertion of Genes Encoding Purine Biosynthesis Related Enzymes Using Vector (pDZ) for Chromosomal Insertion and Development of Strain Producing High Yield of 5'-Inosinic Acid Thereby In order to insert a foreign gene into the chromosome of *Corynebacterium ammoniagenes* strain, a pDZ-based recombinant vector containing two consecutive copies of the corresponding gene was used. The pDZ vector is a vector for chromosomal insertion into the microorganism of the genus *Corynebacterium*, and was prepared by the method disclosed in Korean Patent Publication No. 2008-0025355 incorporated by reference herein. FIG. 1 is a schematic diagram showing the structure of the pDZ vector.

In the following (1) to (6), recombinant vectors were prepared, in which the recombinant vectors function to insert the gene encoding purine biosynthesis related enzyme into the chromosome of the microorganism of the genus *Corynebacterium* to obtain two copies of each gene. Transformation by each recombinant vector and selection of transformants were performed as follows.

The 5'-inosinic acid-producing strain, *Corynebacterium ammoniagenes* CJIP2401 (KCCM-10610) was transformed with the pDZ recombinant vector containing the desired gene encoding purine biosynthesis related enzyme by electroporation, and then strains, in which the gene carried by the vector is inserted into their chromosome by homologous recombination, were selected on a selection medium containing 25 mg/l of kanamycin. The successful chromosomal insertion of the vector was confirmed by the color of the colonies on a solid medium (1% beef extract, 1% yeast extract, 1% peptone, 0.25% sodium chloride, 1% adenine, 1% guanine, 1.5% agarose) containing X-gal (5-bromo-4-chloro-3-indolyl-(β-D-galactoside). That is, blue colonies were selected as a transformant, in which the vector was inserted into the chromosome. The strain, in which the vector was inserted into its chromosome via a first crossover, was shaking-cultured (30° C., 8 hours) in a nutrient medium (1% glucose, 1% beef extract, 1% yeast extract, 1% peptone, 0.25% sodium chloride, 1% adenine, 1% guanine). Then, the cultured strain was serially diluted from $10^{-4}$ to $10^{-10}$, and the diluted culture was plated on a solid medium containing X-gal. Most colonies exhibited blue color, but white colonies also existed at a low level. By selecting the white colonies, strains in which the sequence of the vector was removed from the chromosome via a second crossover were selected. The selected strain was identified as a final strain by a susceptibility test for kanamycin and a gene sequence analysis by PCR.

(1) Cloning of purFM Gene and Construction of Recombinant Vector (pDZ-2purFM)

The purF and purM genes are located close to each other on the chromosome of the microorganism of the genus *Corynebacterium*, and thus a purFM vector containing both of the genes and the promoter region was constructed in order to express both of the genes at the same time.

Figure 2:
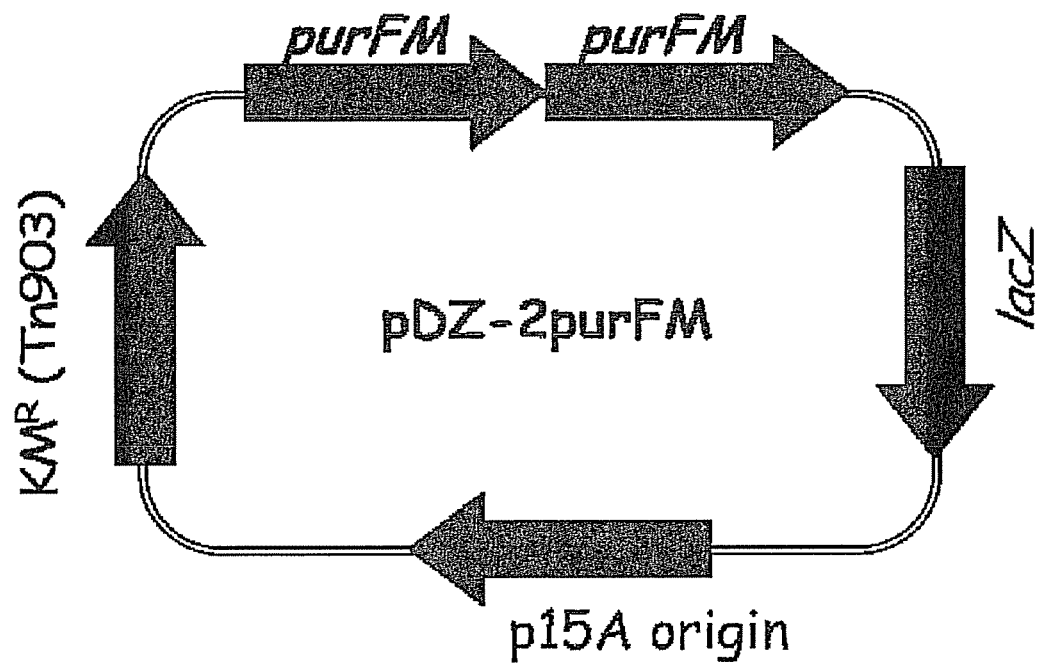
FIG. 2 shows a pDZ-2purFM vector for chromosomal insertion into the microorganism of the genus *Corynebacterium*.

The chromosome was isolated from *Corynebacterium ammoniagenes* CJIP2401 producing 5'-inosinic acid, and Polymerase Chain Reaction (PCR) was performed using the chromosome as a template in order to obtain purFM, namely, a fragment containing the consecutively arranged purF and purM. PfuUltra™ High-Fidelity DNA Polymerase (Stratagene) was used as a polymerase, and Polymerase Chain Reaction was performed with 30 cycles of denaturing at 96° C. for 30 sec, annealing at 53° C. for 30 sec, and polymerization at 72° C. for 2 min. As a result, two purFM genes containing the promoter region (purFM-A, purFM-B) were obtained. The purFM-A was amplified using the primers of SEQ ID NOs. 1 and 2, and the purFM-B was amplified using the primers of SEQ ID NOs. 3 and 4. The amplification products were cloned into an *E. coli* vector pCR2.1 using a TOPO Cloning Kit (Invitrogen) so as to obtain pCR-purFM-A and pCR-purFM-B vectors, respectively. The pCR vectors were treated with restriction enzymes contained in each end of the purFM-A and purFM-B (purFM-A: EcoRI+XbaI, purFM-B: XbaI+HindIII), and each purFM gene was separated from the pCR vectors. Thereafter, the pDZ vector treated with restriction enzymes, EcoRI and HindIII was cloned by 3-piece ligation so as to construct a pDZ-2purFM recombinant vector where two purFM genes are consecutively cloned. FIG. 2 shows a pDZ-2purFM vector for chromosomal insertion into *Corynebacterium*.

The 5'-inosinic acid-producing strain, *Corynebacterium ammoniagenes* CJIP2401 was transformed with the pDZ-2purFM vector by electroporation, and one purFM gene is additionally inserted next to the intrinsic purFM gene on the chromosome via a second crossover, so as to obtain a strain having total two copies. The consecutively inserted purFM genes were identified by PCR using the primers of SEQ ID NOs. 5 and 6 which are able to amplify the regions of connecting two purFM genes.

(2) Cloning of purNH Gene and Construction of Recombinant Vector (pDZ-2purNH), Preparation of purNH-Inserted Strain The purN and purH genes are located close to each other on the chromosome of the microorganism of the genus *Corynebacterium*, and thus a purNH vector containing the promoter region was constructed in order to express both of the genes at the same time.

Figure 3:
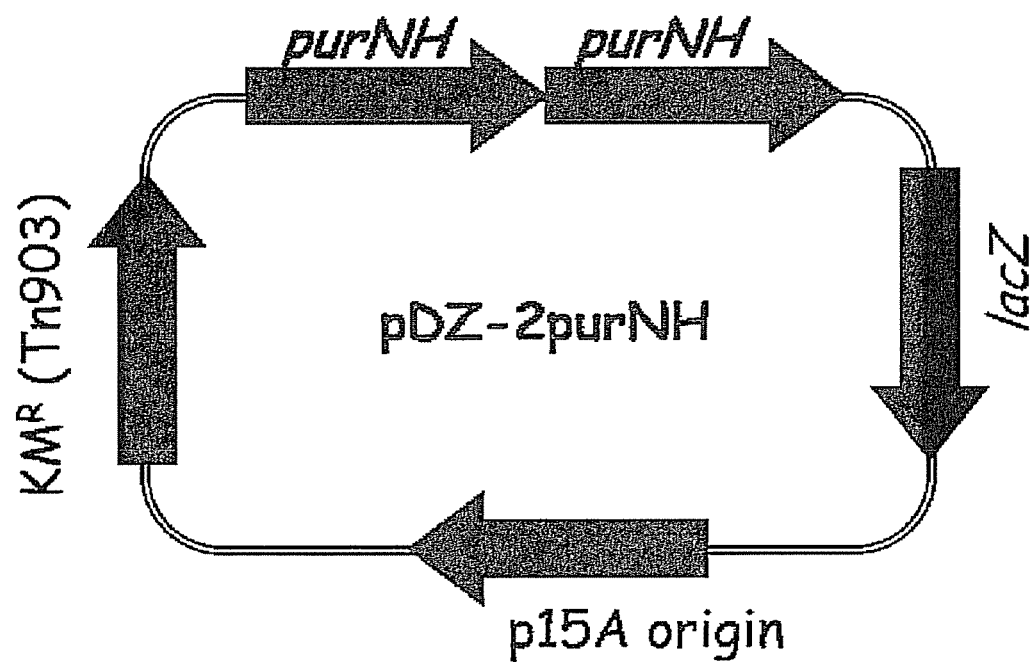
FIG. 3 shows a pDZ-2purNH vector for chromosomal insertion into the microorganism of the genus *Corynebacterium*.

The chromosome was isolated from *Corynebacterium ammoniagenes* CJIP2401 producing 5'-inosinic acid, and Polymerase Chain Reaction (PCR) was performed using the chromosome as a template in order to obtain purNH, namely, a fragment containing the consecutively arranged purN and purH. PfuUltra™ High-Fidelity DNA Polymerase (Stratagene) was used as a polymerase, and Polymerase Chain Reaction was performed with 30 cycles of denaturing at 96° C. for 30 sec, annealing at 53° C. for 30 sec, and polymerization at 72° C. for 2 min. As a result, two purNH genes containing the promoter region (purNH-A, purNH-B) were obtained. The purNH-A was amplified using the primers of SEQ ID NOs. 7 and 8, and the purNH-B was amplified using the primers of SEQ ID NOs. 8 and 9. The amplification products were cloned into an *E. coli* vector pCR2.1 using a TOPO Cloning Kit (Invitrogen) so as to obtain pCR-purNH-A and pCR-purNH-B vectors, respectively. The pCR vectors were treated with restriction enzymes contained in each end of the purNH-A and purNH-B (purNH-A: BamHI+SalI, purNH-B: SalI), and each purNH gene was separated from the pCR vectors. Thereafter, the pDZ vector treated with restriction enzymes, BamHI and SalI was cloned by 3-piece ligation so as to construct a pDZ-2purNH recombinant vector where two purNH genes are consecutively cloned. FIG. 3 shows a pDZ-2purNH vector for chromosomal insertion into *Corynebacterium*.

The 5'-inosinic acid-producing strain, *Corynebacterium ammoniagenes* CJIP2401 was transformed with the pDZ-2purNH vector by electroporation, and one purNH gene is additionally inserted next to the intrinsic purNH gene on the chromosome via a second crossover, so as to obtain a strain having total two copies. The consecutively inserted purNH genes were identified by PCR using the primers of SEQ ID NOs. 10 and 11 which are able to amplify the regions of connecting two purNH genes.

(3) Cloning of purSL Gene and Construction of Recombinant Vector (pDZ-2purSL), Preparation of purSL-Inserted Strain The purS and purL genes are located close to each other on the chromosome of the microorganism of the genus *Corynebacterium*, and thus a purSL vector containing the promoter region was constructed in order to express both of the genes at the same time.

Figure 4:
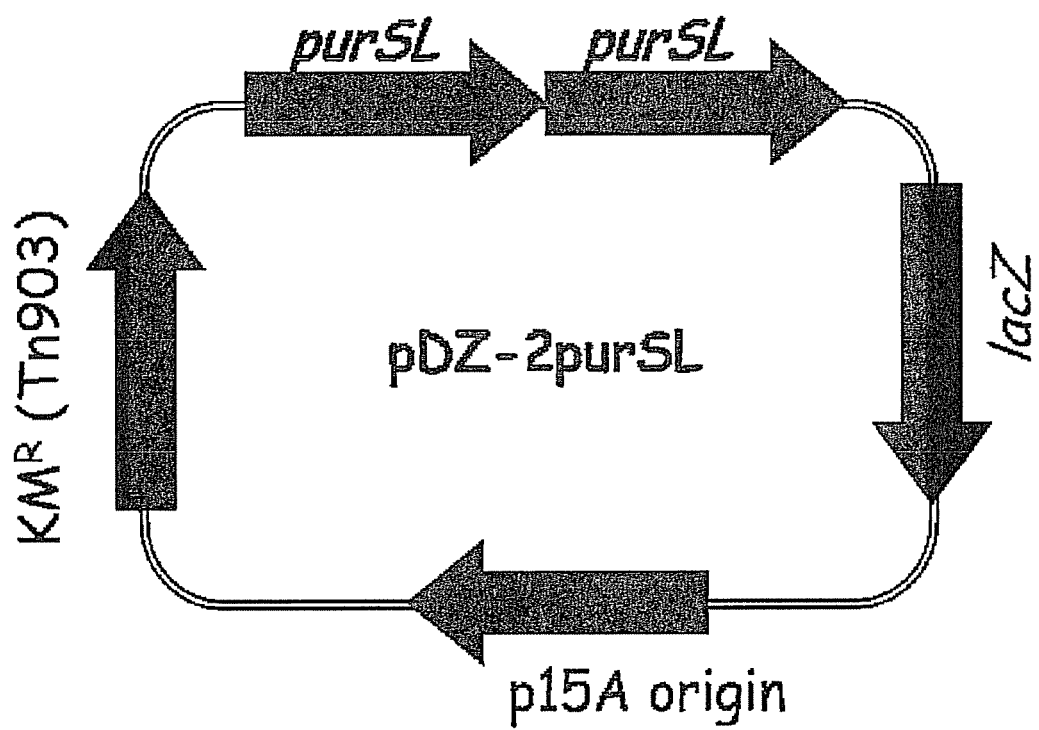
FIG. 4 shows a pDZ-2purSL vector for chromosomal insertion into the microorganism of the genus *Corynebacterium*.

The chromosome was isolated from *Corynebacterium ammoniagenes* CJIP2401 producing 5'-inosinic acid, and Polymerase Chain Reaction (PCR) was performed using the chromosome as a template in order to obtain purSL, namely, a fragment containing the consecutively arranged purS and purL. PfuUltra™ High-Fidelity DNA Polymerase (Stratagene) was used as a polymerase, and Polymerase Chain Reaction was performed with 30 cycles of denaturing at 96° C. for 30 sec, annealing at 53° C. for 30 sec, and polymerization at 72° C. for 2 min. As a result, two purSL genes containing the promoter region (purSL-A, purSL-B) were obtained. The purSL-A was amplified using the primers of SEQ ID NOs. 12 and 13, and the purSL-B was amplified using the primers of SEQ ID NOs. 14 and 15. The amplification products were cloned into an E. coli vector pCR2.1 using a TOPO Cloning Kit (Invitrogen) so as to obtain pCR-purSL-A and pCR-purSL-B vectors, respectively. The pCR vectors were treated with restriction enzymes contained in each end of the purSL-A and purSL-B (purSL-A: BamHI+SalI, purSL-B: SalI+BamHI), and each purSL gene was separated from the pCR vectors. Thereafter, the pDZ vector treated with restriction enzyme, BamHI was cloned by 3-piece ligation so as to construct a pDZ-2purSL recombinant vector where two purSL genes are consecutively cloned. FIG. 4 shows a pDZ-2purSL vector for chromosomal insertion into Corynebacterium.

The 5'-inosinic acid-producing strain, Corynebacterium ammoniagenes CJIP2401 was transformed with the pDZ-2purSL vector by electroporation, and one purSL gene is additionally inserted next to the intrinsic purSL gene on the chromosome via a second crossover, so as to obtain a strain having total two copies. The consecutively inserted purSL genes were identified by PCR using the primers of SEQ ID NOs. 16 and 17 which are able to amplify the regions of connecting two purSL genes.

(4) Cloning of purKE Gene and Construction of Recombinant Vector (pDZ-2purKE), Preparation of purKE-Inserted Strain The purK and purE genes are located close to each other on the chromosome of the microorganism of the genus Corynebacterium, and thus a purKE vector containing the promoter region was constructed in order to express both of the genes at the same time.

Figure 5:
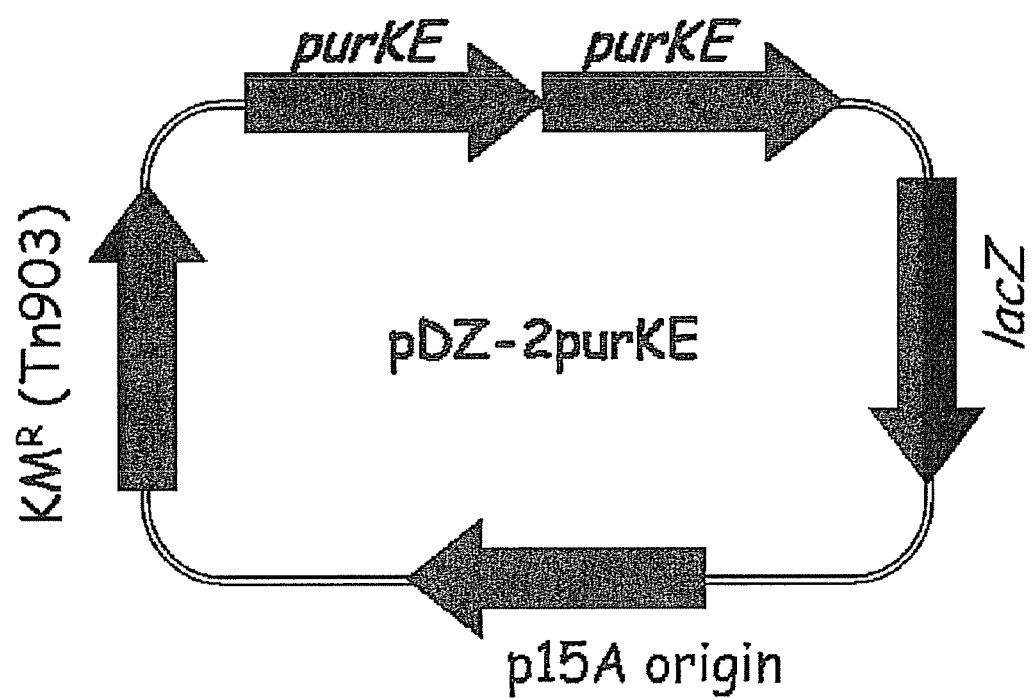
FIG. 5 shows a pDZ-2purKE vector for chromosomal insertion into the microorganism of the genus *Corynebacterium*.

The chromosome was isolated from Corynebacterium ammoniagenes CJIP2401 producing 5'-inosinic acid, and Polymerase Chain Reaction (PCR) was performed using the chromosome as a template in order to obtain purKE, namely, a fragment containing the consecutively arranged purK and purE. PfuUltra™ High-Fidelity DNA Polymerase (Stratagene) was used as a polymerase, and Polymerase Chain Reaction was performed with 30 cycles of denaturing at 96° C. for 30 sec, annealing at 53° C. for 30 sec, and polymerization at 72° C. for 2 min. As a result, two purKE genes containing the promoter region (purKE-A, purKE-B) were obtained. The purKE-A was amplified using the primers of SEQ ID NOs. 18 and 19, and the purKE-B was amplified using the primers of SEQ ID NOs. 20 and 21. The amplification products were cloned into an E. coli vector pCR2.1 using a TOPO Cloning Kit (Invitrogen) so as to obtain pCR-purKE-A and pCR-purKE-B vectors, respectively. The pCR vectors were treated with restriction enzymes contained in each end of the purKE-A and purKE-B (purKE-A: BamHI+KpnI, purKE-B: KpnI+XbaI), and each purKE gene was separated from the pCR vectors. Thereafter, the pDZ vector treated with restriction enzymes, BamHI and XbaI was cloned by 3-piece ligation so as to construct a pDZ-2purKE recombinant vector where two purKE genes are consecutively cloned. FIG. 5 shows a pDZ-2purKE vector for chromosomal insertion into Corynebacterium.

The 5'-inosinic acid-producing strain, Corynebacterium ammoniagenes CJIP2401 was transformed with the pDZ-2purKE vector by electroporation, and one purKE gene is additionally inserted next to the intrinsic purKE gene on the chromosome via a second crossover, so as to obtain a strain having total two copies. The consecutively inserted purKE genes were identified by PCR using the primers of SEQ ID NOs. 22 and 23 which are able to amplify the regions of connecting two purKE genes.

Figure 6:
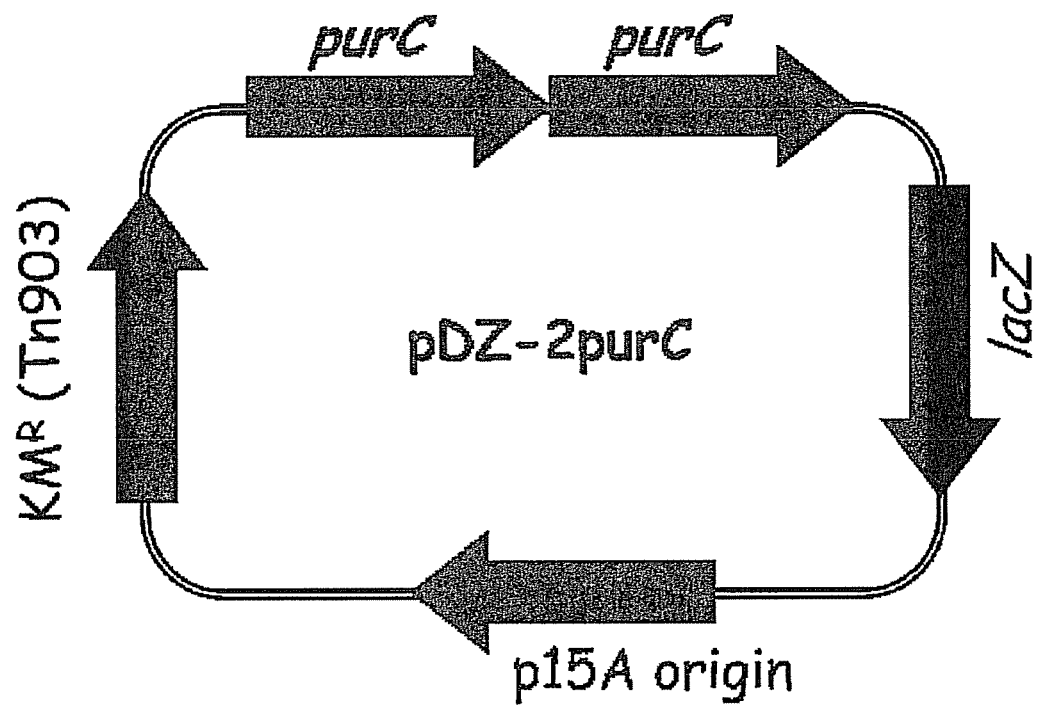
FIG. 6 shows a pDZ-2purC vector for chromosomal insertion into the microorganism of the genus *Corynebacterium*.

(5) Cloning of purC Gene and Construction of Recombinant Vector (pDZ-2purC), Preparation of purC-Inserted Strain The chromosome was isolated from Corynebacterium ammoniagenes CJIP2401, and Polymerase Chain Reaction (PCR) was performed using the chromosome as a template in order to obtain purC. PfuUltra™ High-Fidelity DNA Polymerase was used as a polymerase, and Polymerase Chain Reaction was performed with 30 cycles of denaturing at 96° C. for 30 sec, annealing at 53° C. for 30 sec, and polymerization at 72° C. for 2 min. As a result, two purC genes containing the promoter region (purC-A, purC-B) were obtained. The purC-A was amplified using the primers of SEQ ID NOs. 24 and 25, and the purC-B was amplified using the primers of SEQ ID NOs. 25 and 26. The amplification products were cloned into an E. coli vector pCR2.1 using a TOPO Cloning Kit so as to obtain pCR-purC-A and pCR-purC-B vectors, respectively. The pCR vectors were treated with restriction enzymes contained in each end of the purC-A and purC-B (purC-A: BamHI+SalI, purC-B: SalI), and each purC gene was separated from the pCR vectors. Thereafter, the pDZ vector treated with restriction enzymes, BamHI and SalI was cloned by 3-piece ligation so as to construct a pDZ-2purC recombinant vector where two purC genes are consecutively cloned. FIG. 6 shows a pDZ-2purC vector for chromosomal insertion into Corynebacterium.

The 5'-inosinic acid-producing strain, Corynebacterium ammoniagenes CJIP2401 was transformed with the pDZ-2purC vector by electroporation, and one purC gene is additionally inserted next to the intrinsic purC gene on the chromosome via a second crossover, so as to obtain a strain having total two copies. The consecutively inserted purC genes were identified by PCR using the primers of SEQ ID NOs. 27 and 28 which are able to amplify the regions of connecting two purC genes.

Figure 7:
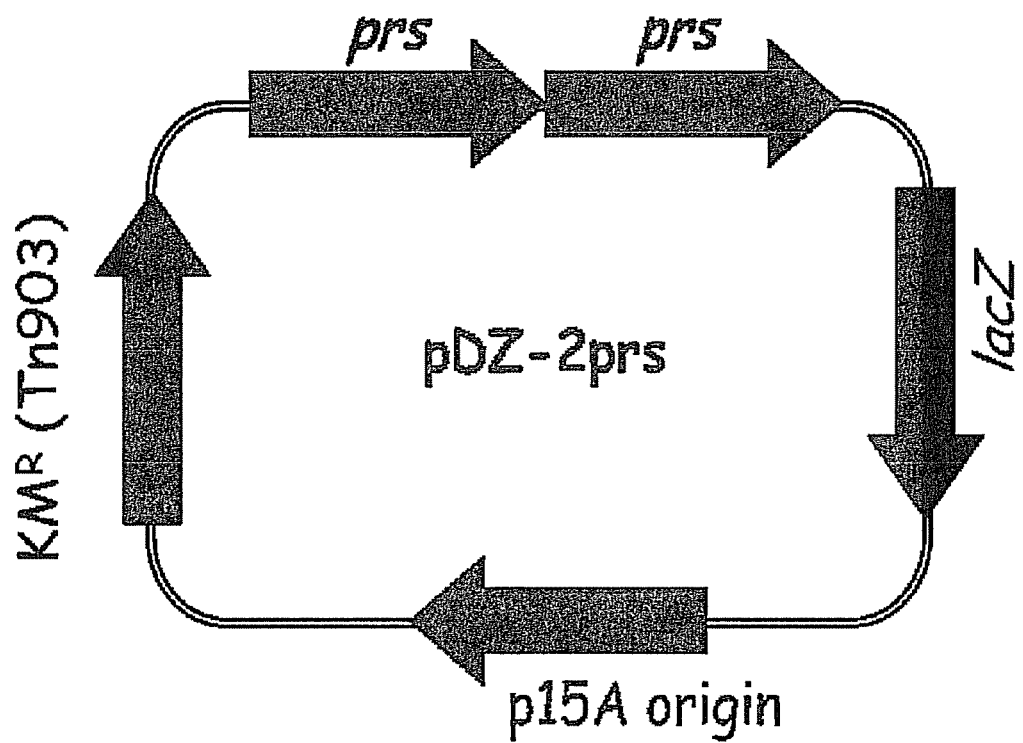
FIG. 7 shows a pDZ-2prs vector for chromosomal insertion into the microorganism of the genus *Corynebacterium*.

(6) Cloning of prs Gene and Construction of Recombinant Vector (pDZ-2prs), Preparation of prs-Inserted Strain The chromosome was isolated from Corynebacterium ammoniagenes CJIP2401, and Polymerase Chain Reaction (PCR) was performed using the chromosome as a template in order to obtain prs. PfuUltra™ High-Fidelity DNA Polymerase was used as a polymerase, and Polymerase Chain Reaction was performed with 30 cycles of denaturing at 96° C. for 30 sec, annealing at 53° C. for 30 sec, and polymerization at 72° C. for 2 min. As a result, two prs genes containing the promoter region (prs-A, prs-B) were obtained. The prs-A was amplified using the primers of SEQ ID NOs. 29 and 30, and the prs-B was amplified using the primers of SEQ ID NOs. 31 and 32. The amplification products were cloned into an E. coli vector pCR2.1 using a TOPO Cloning Kit so as to obtain pCR-prs-A and pCR-prs-B vectors, respectively. The pCR vectors were treated with restriction enzymes contained in each end of the prs-A and prs-B (prs-A: BamHI+SpeI, prs-B: SpeI+PstI), and each prs gene was separated from the pCR vectors. Thereafter, the pDZ vector treated with restriction enzymes, BamHI and PstI was cloned by 3-piece ligation so as to construct a pDZ-2prs recombinant vector where two prs genes are consecutively cloned. FIG. 7 shows a pDZ-2prs vector for chromosomal insertion into *Corynebacterium*.

The 5'-inosinic acid-producing strain, *Corynebacterium ammoniagenes* CJIP2401 was transformed with the pDZ-2prs vector by electroporation, and one prs gene is additionally inserted next to the intrinsic prs gene on the chromosome via a second crossover, so as to obtain a strain having total two copies. The consecutively inserted prs genes were identified by PCR using the primers of SEQ ID NOs. 33 and 34 which are able to amplify the regions of connecting two prs genes.

(7) Development of Strain Producing High Yield of 5'-Inosinic Acid by Enhancement of Purine Biosynthesis Combinations of pDZ-2purFM, pDZ-2purNH, pDZ-2purSL, pDZ-2purKE, pDZ-2purC, and pDZ-2prs vectors constructed in (1) to (6) were introduced into the 5'-inosinic acid-producing *Corynebacterium ammoniagenes* CJIP2401. The introduction, order of the vectors was randomly selected, and introduction method and identification are the same as the above.

The *Corynebacterium ammoniagenes* CJIP2401 was used as a parental strain, and transformed with a combination of pDZ-2purNH, pDZ-2purSL, pDZ-2purKE, pDZ-2purC, and pDZ-2prs, and a combination of pDZ-2purNH, pDZ-2purSL, pDZ-2purKE, pDZ-2purC, pDZ-2purFM and pDZ-2prs to obtain *Corynebacterium ammoniagenes* CN01-0120 (2purNH+2purSL+2purKE+2purC+2prs) and *Corynebacterium ammoniagenes* CN01-0316 (2purNH+2purSL+2purKE+2purC+2purFM+2prs), which contain two copies of the genes encoding the major enzymes involved in the purine biosynthetic pathway.

EXAMPLE 2

Fermentation Titer Test of Recombinant *Corynebacterium ammoniagenes*

Each 3 ml of the seed medium with the following composition was distributed into test tubes having a diameter of 18 mm, and sterilized under pressure. Then, the parental strain *Corynebacterium ammoniagenes* CJ1P2401, and the *Corynebacterium ammoniagenes* CN01-0120 and *Corynebacterium ammoniagenes* CN01-0316 prepared in Example 1 were inoculated, and shaking-cultured at 30° C. for 24 hours to be used as a seed culture. Each 27 ml of the fermentation medium with the following composition was distributed into 500 ml Erlenmeyer shake flasks and sterilized under pressure at 120° C. for 10 minutes, and each 3 ml of the seed culture was inoculated thereto and shaking-cultured for 5 to 6 days. The cultivation was carried out under the conditions of 200 rpm, 32° C., and pH 7.2

The seed medium and the fermentation medium have the following compositions.

Seed Medium:
1% glucose, 1% peptone, 1% beef extract, 1% yeast extract, 0.25% sodium chloride, 100 mg/l adenine, 100 mg/l guanine, pH7.2

Flask Fermentation Medium:
0.1% sodium glutamate, 1% ammonium chloride, 1.2% magnesium sulfate, 0.01% calcium chloride, 20 mg/l iron sulfate, 20 mg/l manganese sulfate, 20 mg/l zinc sulfate, 5 mg/l copper sulfate, 23 mg/l L-cysteine, 24 mg/l alanine, 8 mg/l nicotinic acid, 45 μg/l biotin, 5 mg/l thiamine hydrochloride, 30 mg/l adenine, 1.9% phosphoric acid (85%), 4.2% glucose, and 2.4% raw sugar After completion of the cultivation, the productivity of 5'-inosinic acid was measured by HPLC, and the accumulation amount of 5'-inosinic acid in the culture medium is shown in the following Table.

TABLE 1

| Strain name | Cell OD (5 days after culture) | Productivity (g/l/hr) (5 days after culture) |
|---|---|---|
| Control group (CJIP2401) | 31.2 | 0.136 |
| CN01-0120 | 31.8 | 0.155 |
| CN01-0316 | 31.3 | 0.149 |

The accumulation amount of 5'-inosinic acid in the culture medium was compared with that of the parental strain, *Corynebacterium ammoniagenes* CJIP2401. As a result, in *Corynebacterium ammoniagenes* CN01-0120 and *Corynebacterium ammoniagenes* CN01-0316, their 5'-inosinic acid productivity per hour was found to be increased to 10.9-11.4% under the same conditions, compared to the parental strain, *Corynebacterium ammoniagenes* CJIP2401.

*Corynebacterium ammoniagenes* CN01-0316 having improved 5'-inosinic acid productivity by increasing the activity of purine biosynthesis related enzymes was deposited in the Korean Culture Center of Microorganisms (KCCM) located at Hongje 1-dong, Seodaemun-gu, Seoul, with the Accession No. KCCM 10992P on Feb. 19, 2009 under the Budapest treaty.

Effect of the Invention

The microorganism belonging to the genus *Corynebacterium* producing 5'-inosinic acid according to the present invention, in which the expression of gene encoding purine biosynthesis related enzymes is increased higher than the intrinsic expression, can be used to produce 5'-inosinic acid in a high concentration and a high yield, thereby reducing production costs.

What is claimed is:

1. An isolated recombinant microorganism belonging to the genus *Corynebacterium* that produces 5'inosinic acid, wherein the microorganism is *Corynebacterium ammoniagenes* CN01-0316 (KCCM 10992P).

2. A method for producing 5'-inosinic acid comprising culturing the isolated recombinant microorganism according to claim 1 and recovering 5'-inosinic acid from the culture medium.

SEQUENCE LISTING

```
<160> NUMBER OF SEQ ID NOS: 43

<210> SEQ ID NO 1
<211> LENGTH: 30
<212> TYPE: DNA
<213> ORGANISM: Artificial Sequence
<220> FEATURE:
<223> OTHER INFORMATION: Primer for purFM

<400> SEQUENCE: 1
cgacgagaat tccccgaccc gcatgagatg                              30
```

```
<210> SEQ ID NO 2
<211> LENGTH: 30
<212> TYPE: DNA
<213> ORGANISM: Artificial Sequence
<220> FEATURE:
<223> OTHER INFORMATION: Primer for purFM

<400> SEQUENCE: 2
gtatcgtcta gagcggtagc ggtggcttcg                                   30

<210> SEQ ID NO 3
<211> LENGTH: 30
<212> TYPE: DNA
<213> ORGANISM: Artificial Sequence
<220> FEATURE:
<223> OTHER INFORMATION: Primer for purFM

<400> SEQUENCE: 3
cgacgatcta gacccgaccc gcatgagatg                                   30

<210> SEQ ID NO 4
<211> LENGTH: 30
<212> TYPE: DNA
<213> ORGANISM: Artificial Sequence
<220> FEATURE:
<223> OTHER INFORMATION: Primer for purFM

<400> SEQUENCE: 4
gtatcgaagc ttgcggtagc ggtggcttcg                                   30

<210> SEQ ID NO 5
<211> LENGTH: 18
<212> TYPE: DNA
<213> ORGANISM: Artificial Sequence
<220> FEATURE:
<223> OTHER INFORMATION: Primer for 2purFM

<400> SEQUENCE: 5
gctatcgttt cccctgaa                                                18

<210> SEQ ID NO 6
<211> LENGTH: 18
<212> TYPE: DNA
<213> ORGANISM: Artificial Sequence
<220> FEATURE:
<223> OTHER INFORMATION: Primer for 2purFM

<400> SEQUENCE: 6
tgattctact aagtttgc                                                18

<210> SEQ ID NO 7
<211> LENGTH: 34
<212> TYPE: DNA
<213> ORGANISM: Artificial Sequence
<220> FEATURE:
<223> OTHER INFORMATION: Primer for purNH

<400> SEQUENCE: 7
cgggatcccg aggcgaagac gatattgagg acag                              34

<210> SEQ ID NO 8
<211> LENGTH: 32
<212> TYPE: DNA
<213> ORGANISM: Artificial Sequence
<220> FEATURE:
<223> OTHER INFORMATION: Primer for purNH
```

<400> SEQUENCE: 8
acgcgtcgac gtgggaaacg cagacgagaa ca                                    32

<210> SEQ ID NO 9
<211> LENGTH: 35
<212> TYPE: DNA
<213> ORGANISM: Artificial Sequence
<220> FEATURE:
<223> OTHER INFORMATION: Primer for purNH

<400> SEQUENCE: 9
acgcgtcgac gaggcgaaga cgatattgag gacag                                 35

<210> SEQ ID NO 10
<211> LENGTH: 18
<212> TYPE: DNA
<213> ORGANISM: Artificial Sequence
<220> FEATURE:
<223> OTHER INFORMATION: Primer for 2purNH

<400> SEQUENCE: 10
tcgatgcctg catcttgg                                                    18

<210> SEQ ID NO 11
<211> LENGTH: 18
<212> TYPE: DNA
<213> ORGANISM: Artificial Sequence
<220> FEATURE:
<223> OTHER INFORMATION: Primer for 2purNH

<400> SEQUENCE: 11
ggcgataagg cttcgagt                                                    18

<210> SEQ ID NO 12
<211> LENGTH: 46
<212> TYPE: DNA
<213> ORGANISM: Artificial Sequence
<220> FEATURE:
<223> OTHER INFORMATION: Primer for purSL

<400> SEQUENCE: 12
gctcggatcc gcgatactca gccccagcaa cagcagaaaa tgaagc                     46

<210> SEQ ID NO 13
<211> LENGTH: 39
<212> TYPE: DNA
<213> ORGANISM: Artificial Sequence
<220> FEATURE:
<223> OTHER INFORMATION: Primer for purSL

<400> SEQUENCE: 13
cagcgtcgac gcagccgtcg caggcaccat cgcagcagt                             39

<210> SEQ ID NO 14
<211> LENGTH: 46
<212> TYPE: DNA
<213> ORGANISM: Artificial Sequence
<220> FEATURE:
<223> OTHER INFORMATION: Primer for purSL

<400> SEQUENCE: 14
cagcgtcgac gcgatactca gccccagcaa cagcagaaaa tgaagc                     46

```
<210> SEQ ID NO 15
<211> LENGTH: 39
<212> TYPE: DNA
<213> ORGANISM: Artificial Sequence
<220> FEATURE:
<223> OTHER INFORMATION: Primer for purSL

<400> SEQUENCE: 15
gctcggatcc gcagccgtcg caggcaccat cgcagcagt                    39

<210> SEQ ID NO 16
<211> LENGTH: 18
<212> TYPE: DNA
<213> ORGANISM: Artificial Sequence
<220> FEATURE:
<223> OTHER INFORMATION: Primer for 2purSL

<400> SEQUENCE: 16
acttgacctc cagcccta                                           18

<210> SEQ ID NO 17
<211> LENGTH: 18
<212> TYPE: DNA
<213> ORGANISM: Artificial Sequence
<220> FEATURE:
<223> OTHER INFORMATION: Primer for 2purSL

<400> SEQUENCE: 17
aagaacaacg tcggcgtc                                           18

<210> SEQ ID NO 18
<211> LENGTH: 30
<212> TYPE: DNA
<213> ORGANISM: Artificial Sequence
<220> FEATURE:
<223> OTHER INFORMATION: Primer for purKE

<400> SEQUENCE: 18
acgtcaggat cccctatcgt gctttgctgt                              30

<210> SEQ ID NO 19
<211> LENGTH: 30
<212> TYPE: DNA
<213> ORGANISM: Artificial Sequence
<220> FEATURE:
<223> OTHER INFORMATION: Primer for purKE

<400> SEQUENCE: 19
ctctaaggta ccattggtac tagtagccgc                              30

<210> SEQ ID NO 20
<211> LENGTH: 30
<212> TYPE: DNA
<213> ORGANISM: Artificial Sequence
<220> FEATURE:
<223> OTHER INFORMATION: Primer for purKE

<400> SEQUENCE: 20
acgtcaggta cccctatcgt gctttgctgt                              30

<210> SEQ ID NO 21
<211> LENGTH: 30
<212> TYPE: DNA
<213> ORGANISM: Artificial Sequence
<220> FEATURE:
<223> OTHER INFORMATION: Primer for purKE
```

```
<400> SEQUENCE: 21
ctctaatcta gaattggtac tagtagccgc                               30

<210> SEQ ID NO 22
<211> LENGTH: 18
<212> TYPE: DNA
<213> ORGANISM: Artificial Sequence
<220> FEATURE:
<223> OTHER INFORMATION: Primer for 2purKE

<400> SEQUENCE: 22
ccagctgggg ttccggtt                                            18

<210> SEQ ID NO 23
<211> LENGTH: 18
<212> TYPE: DNA
<213> ORGANISM: Artificial Sequence
<220> FEATURE:
<223> OTHER INFORMATION: Primer for 2purKE

<400> SEQUENCE: 23
tttcgatgcg cttcgttt                                            18

<210> SEQ ID NO 24
<211> LENGTH: 37
<212> TYPE: DNA
<213> ORGANISM: Artificial Sequence
<220> FEATURE:
<223> OTHER INFORMATION: Primer for purC

<400> SEQUENCE: 24
gctcggatcc cgcagtggct gttgcgctga acatgcg                       37

<210> SEQ ID NO 25
<211> LENGTH: 39
<212> TYPE: DNA
<213> ORGANISM: Artificial Sequence
<220> FEATURE:
<223> OTHER INFORMATION: Primer for purC

<400> SEQUENCE: 25
gcaggtcgac cacggacata tcggtttgct tcacgcggg                     39

<210> SEQ ID NO 26
<211> LENGTH: 37
<212> TYPE: DNA
<213> ORGANISM: Artificial Sequence
<220> FEATURE:
<223> OTHER INFORMATION: Primer for purC

<400> SEQUENCE: 26
gcaggtcgac cgcagtggct gttgcgctga acatgcg                       37

<210> SEQ ID NO 27
<211> LENGTH: 24
<212> TYPE: DNA
<213> ORGANISM: Artificial Sequence
<220> FEATURE:
<223> OTHER INFORMATION: Primer for 2purC

<400> SEQUENCE: 27
gagcgcttgt ccggcaagcg tttc                                     24
```

```
<210> SEQ ID NO 28
<211> LENGTH: 24
<212> TYPE: DNA
<213> ORGANISM: Artificial Sequence
<220> FEATURE:
<223> OTHER INFORMATION: Primer for 2purC

<400> SEQUENCE: 28
ggtggttgcg gtaagaaccc ggcc                                              24

<210> SEQ ID NO 29
<211> LENGTH: 33
<212> TYPE: DNA
<213> ORGANISM: Artificial Sequence
<220> FEATURE:
<223> OTHER INFORMATION: Primer for prs

<400> SEQUENCE: 29
gctcggatcc ggattcccaa gcttgcttcc ggg                                    33

<210> SEQ ID NO 30
<211> LENGTH: 36
<212> TYPE: DNA
<213> ORGANISM: Artificial Sequence
<220> FEATURE:
<223> OTHER INFORMATION: Primer for prs

<400> SEQUENCE: 30
cagcactagt ggcagctacc acctccgcgg ctgctg                                 36

<210> SEQ ID NO 31
<211> LENGTH: 33
<212> TYPE: DNA
<213> ORGANISM: Artificial Sequence
<220> FEATURE:
<223> OTHER INFORMATION: Primer for prs

<400> SEQUENCE: 31
cagcactagt ggattcccaa gcttgcttcc ggg                                    33

<210> SEQ ID NO 32
<211> LENGTH: 37
<212> TYPE: DNA
<213> ORGANISM: Artificial Sequence
<220> FEATURE:
<223> OTHER INFORMATION: Primer for prs

<400> SEQUENCE: 32
caattctgca gggcagctac cacctccgcg gctgctg                                37

<210> SEQ ID NO 33
<211> LENGTH: 23
<212> TYPE: DNA
<213> ORGANISM: Artificial Sequence
<220> FEATURE:
<223> OTHER INFORMATION: Primer for 2prs

<400> SEQUENCE: 33
cgtacgattc atgagatctt cga                                               23

<210> SEQ ID NO 34
<211> LENGTH: 21
<212> TYPE: DNA
<213> ORGANISM: Artificial Sequence
<220> FEATURE:
<223> OTHER INFORMATION: Primer for 2prs
```

```
<400> SEQUENCE: 34
caaagtcacg ggcggtggta g                                           21

<210> SEQ ID NO 35
<211> LENGTH: 1500
<212> TYPE: DNA
<213> ORGANISM: Corynebacterium ammoniagenes
<220> FEATURE:
<221> NAME/KEY: gene
<222> LOCATION: (1)..(1500)
<223> OTHER INFORMATION: purF

<400> SEQUENCE: 35
gtggtgaaca ctactttccc cagcgacgtg aatttagatg accaaggcga gcaagaaccc      60
cgcgaagagt gcggtgtctt tggcgtctgg gctcctggtg aagatgttgc gacactgacc     120
tactttggtc tgttcgcatt gcagcatcgt gggcaggaag ctgcaggtat cggcgtcggt     180
gatggagacc gcctcgttgt cttcaaagac atgggcttgg tctcgaatat tttcgatgag     240
tccattttaa attccctcca tggctccgtg gcgtggggc atacgcgcta ctcgactgcc      300
ggtggcaaag agtggtcgaa tgtccagccg atgtttaata ccacctcaaa tggggtagac     360
atcgctttgt gccacaacgg caacttggtg aactaccaag aactgcgcga tgaagcagta     420
gctctgggac tttaccgaga gaatgaaaaa tccctgtcgg attccatgat catgacagct     480
ttgctggcgc acggagtcgg ggaaggcaac tctgtctttg acgccgctaa gcaactgctg     540
ccaagcatca aggcgctttt tgcttgacc tttaccgatg caagaccttt gtacgccgcg      600
cgtgacccgc acggtgtacg ccccttggtc attggccgct tggcgcaagg ctgggttgtt     660
gcttccgaaa cctgtgcgct ggatatcgtg ggcgcacagt ttatccgtga ggtagagccc     720
ggtgaactta tctctgtcaa tgaggcagga atccacagcg aaaaattcgc tgagccgaag     780
cgccagggct gcgtctttga atacgtctac ttggcacgtc agacaccgt gatcaaaggc      840 cgcaacgttc acgcgacgcg cgtggatatt ggtcgcgcac ttgcgaaatc tcaccctgcg     900
ccagaagctg acatggtcat ccccgtgcca gaatccggaa accggcagc tgttggctac      960 gcccgggaat cgggcctgac atttgcgcac ggcttggtca aaaacgccta cgtgggtcga    1020
accttcattc agcccaccca gaccttgcgc cagctggta ttcgcctcaa gctcaacccc     1080
ctgcgcgagg tcatcgaggg caagtcactc gttgttgtag atgactctat tgtccgcggc    1140
aacacccaac gcgcgctggt gcgcatgctg cgtgaagcag gcgctgctga agtgcacgtg    1200
cgcattgctt caccgccagt caaatggcct tgtttctacg gcattgactt cgcctcgcct    1260
ggtgaattga ttgctaatat caagccttct gatgatcctc aggtagtaac cgatgcagtg    1320
tgcgaagcta tcggagcaga ctcttttaggg tttgtatctg tagatgagat ggttgaggca    1380
acgcaccaac ctatcaattc cttgtgtacc gcttgctttg atggcaacta cgaactcgga    1440
cttccgaccg ctaaccccaa tgctgacgct gtgcgaactt tgctcagcca aaagaactga    1500

<210> SEQ ID NO 36
<211> LENGTH: 606
<212> TYPE: DNA
<213> ORGANISM: Corynebacterium ammoniagenes
<220> FEATURE:
<221> NAME/KEY: gene
<222> LOCATION: (1)..(606)
<223> OTHER INFORMATION: purN
```

<400> SEQUENCE: 36

```
gtgactgaat cgccttcgca agttttgaaa gcacaagacc cgcttcaagt agtggtgctg    60
gtatctggca ccggatcttt gctgcaaaat attatcgaca accaagatga ctcctatcgg   120
gttatcaagg tagtcgcgga taagccctgc ccggggatta accgagccca agatgcaggc   180
atcgacaccg aagtcgtgct tttaggctca gaccgcgcgc agtggaacaa agaccttgtc   240
gcagcggttg gtaccgccga tgttgtggtg tccgctggat ttatgaaaat cctggggcct   300
gaattcttgg ccagctttga aggccgcaca ataaatacgc atcccgcact cctgccgtcc   360
tttccgggcg cgcatggagt acgggatgcg ttggcttatg gcgtgaaagt caccggctct   420
actgtccatt ttgtggacgc gggagtcgat actggccgca tcatcgcaca acgcgcagta   480
gagattgagg cagaagatga tgaggcaagc ttgcatgagc gcatcaaaag cgtcgaacgt   540
gagcttatcg tgcaggtctt acgcgcagcg aatgttcaag ccagcagct tattattgag    600
atttaa                                                              606
```

<210> SEQ ID NO 37
<211> LENGTH: 243
<212> TYPE: DNA
<213> ORGANISM: Corynebacterium ammoniagenes
<220> FEATURE:
<221> NAME/KEY: gene
<222> LOCATION: (1)..(243)
<223> OTHER INFORMATION: purS

<400> SEQUENCE: 37

```
atggctcgtg ttgttgtcaa tgtcatgccc aaggctgaaa tcctcgaccc gcagggacaa    60
gctgttgtcc gtgcacttgg acgcctgggt gtaaacggag taagcgatgt ccgtcagggc   120
aagcgctttg aaatcgaagt cgatgattca gtcagcgctg aagatctaga caaggtcgca   180
gcaagcttgc tggcaaacac cgtcatcgag gactacgaag ttgtagggct ggaggtcaag   240
taa                                                                 243
```

<210> SEQ ID NO 38
<211> LENGTH: 2277
<212> TYPE: DNA
<213> ORGANISM: Corynebacterium ammoniagenes
<220> FEATURE:
<221> NAME/KEY: gene
<222> LOCATION: (1)..(2277)
<223> OTHER INFORMATION: purL

<400> SEQUENCE: 38

```
atgactgttt ccaatgacac agtagataat gcaaaggcca ctcccgagct agaccagccg    60
tgggaagaac tcggcttaaa gcaagacgaa tacgacaaga ttgtaggcat cttgggccgc   120
cgcccaaccg atgctgagct gacggtttac tccgtgatgt ggtcggagca ctgctcttac   180
aagtcttcca gacccacct acgctacttt ggcgagacca ccactgagga aatggcgtcg   240
aagattcttg ccggtatcgg tgagaacgct ggtgtcgttg acatcggcga cggtgacgca   300
gtgaccttcc gcgtcgaatc ccacaaccac ccatccttcg tcgagcctta ccagggtgcc   360
gcgaccggtg ttggcggcat cgtccgcgac atcatggcga tgggtgcacg tccaatcgca   420
gtgatggatc agctgcgctt cggcccagct gatgccccgg ataccgcacg tgttctgccg   480
ggcgttgttt ccggcatcgg cggttacggc aactccctcg gcctgccgaa catcggcggc   540
gagaccgtct tgatgagtc ttatgccggc aaccccactgg tcaacgcact gtgcgtgggt   600
accttgcgcg tggaagacct gaagctggct tttgcttccg gtactggcaa caaggtgatg   660
```

| | | |
|---|---|---|
| ctctttggct cccgcacggg cctcgacggc atcggcggcg tatccgtttt gggttctgct | 720 |
| tccttcgaag aaggcgaaga gcgcaagctt cctgcagtcc aggtcggcga cccattcgcg | 780 |
| gaaaaagtcc tcatcgaatg ctgcctggag ctctacgctg cgggcgtcgt tgtcggtatt | 840 |
| caggaccttg gtggcggtgg cctcgcatgt gcgacctctg agctggcagc agctggcgac | 900 |
| ggcggcatgg tggtcaacct ggataatgtt ccactgcgtg cagagaacat gtccgccgca | 960 |
| gaaatcctgg cttccgaatc ccaggagcgc atgtgtgctg ttgtctcccc agataacgtg | 1020 |
| gagaagttcc gcgagatctg tgaaaagtgg gacgtaacgt gtgctgaaat cggtgaagtt | 1080 |
| accgataaga aagacaccta cctcgtgtac cacaacggtg agctggtagt agacgctccg | 1140 |
| ccatcaacta tcgatgaagg ccctgtctac gagcgcccat acgcacgccc tcagtggcag | 1200 |
| gatgagatcc agcaggctcc ggaaattgca cgtccggaat ccttggtaca ggcattcaag | 1260 |
| gacatggtgt cctccccagc tctgtcatcg cgtgcattta tcactgagca gtatgaccgc | 1320 |
| tacgtgcgcg gtaacaccgt caaggcgaag cagtctgact ccggcgttct gcgtatcaat | 1380 |
| gaggaaactt ctcgcggtgt cgcaatttct gccgatgcct ccggtcgcta caccaagctg | 1440 |
| gacccaaaca tgggtgcacg tttggcgctg gctgaggcat accgcaacgt tgctgtgacc | 1500 |
| ggcgcacgac catatgcggt gaccaactgc ttgaacttcg gttctccaga aaacaccgac | 1560 |
| gtgatgtggc aattccgcga ggccgttcac ggtctggctg acggttctaa ggaactgaat | 1620 |
| atcccagtct ccgcggtaa cgtctccttc tacaaccaga ctggtgatga gccaattctg | 1680 |
| ccgaccccag ttgttggcgt gctcggtgtc attgatgatg ttcacaaggc actggcacat | 1740 |
| gacttgggcg gcattgatga gcctgaaacc ctgattctgc ttggtgagac caaggaagaa | 1800 |
| ttcggcggct ccatctggca gcaggtctcc ggcggcggcc tgcagggtct gccaccacag | 1860 |
| gtggatctgg cgaatgaggc aaagctggcg gacttcttcg tcggcaacac ctccgttgca | 1920 |
| gcctcccacg acctctctga gggcggtctg gctatcgcgg cgtttgagat ggcgcaaaag | 1980 |
| aacaacgtcg gcgtcgacct tgatttgagc gttgtacacg aggatgcact gaccgcactg | 2040 |
| tttagtgagt ccgcatcgcg tgttctgatt tccaccgcgt ctgaccacct cgatggaatc | 2100 |
| ttgcagcgtg cttccgagct gggcattcca gctgtcgtgg taggaaccac caatgattcc | 2160 |
| ggcaacatca ccttcgctgg tgaagaagtt gctaccgctg agctgcgcga ggcatggtct | 2220 |
| gcaaccttgc caaacctgtt tggccacgct gttggcgcta attccgtagt cgaataa | 2277 |

<210> SEQ ID NO 39
<211> LENGTH: 1056
<212> TYPE: DNA
<213> ORGANISM: Corynebacterium ammoniagenes
<220> FEATURE:
<221> NAME/KEY: gene
<222> LOCATION: (1)..(1056)
<223> OTHER INFORMATION: purM

<400> SEQUENCE: 39

| | | |
|---|---|---|
| atgtctgaaa atacttacgc cgcggcaggc gtcaacattg aagaaggcga ccgcgccgtt | 60 |
| gagcttttcg ctccactggc taagcgcgct acccgtccag aggtaatggg tggactcggt | 120 |
| ggcttcgcgg gactgtttaa gctcggcgaa tacaaagagc caatccttgc agctggctcc | 180 |
| gacggcgtgg gcaccaagct cgccgttgcc caggcaatgg ataagcacga caccatcggc | 240 |
| attgacctgg ttgcaatgtg cgtcgatgac ttggtcgtgt gtggtgctga gccactattt | 300 |
| ctccaggact acatcgcagt aggcaaggtt gttccggaaa aggttgcgca gattgttgcc | 360 |
| ggtattgctg agggctgcgt gcaggcaggc tgtgcacttc ttggtggcga gaccgctgag | 420 |

```
cacccgggcg taatgaatga aaaggactac gatgtttccg ccaccgctgt cggcgttgtc    480
gaagcagacg agcttctcgg accagacaag gttcgcgacg gcgatgtttt gattgccatg    540
ggctcatccg gactgcactc caatggttac tccttggcgc gccacgtctt gttagagcag    600
gcaggattgc cgctcgatgg ctacatcgat gaccttggcc gcacgcttgg tgaagagctc    660
ctggagccga cccgcatcta cgccaaggac tgcctggcgc tagtttctga gtgtgacgtt    720
gctactttct gccacgtcac cggcggtggc ttggcaggca acctcgagcg cgtgctacct    780
gaaggccttg tcgcagaggt taaccgcgca tcgtggaccc cagcagcgat tttccgcacc    840
atcgcgtctt tcggcaaggt cagcctggaa gagatggaaa agaccttcaa catgggcgtt    900
ggcatgatcg ctatcgtttc ccctgaagac cgtgaccgcg ccttggcgat gctaactgcg    960
cgccacgttg atgcatggga gctgggctcg gttcgcacca agaaggaaga cgacaccgca   1020
ggtgttgtca tgcaaggtga gcactctaac ttctaa                             1056

<210> SEQ ID NO 40
<211> LENGTH: 1779
<212> TYPE: DNA
<213> ORGANISM: Corynebacterium ammoniagenes
<220> FEATURE:
<221> NAME/KEY: gene
<222> LOCATION: (1)..(1779)
<223> OTHER INFORMATION: purKE

<400> SEQUENCE: 40
atgaaacgcg tgagtgaaca agcaggaaac ccagacggaa accctcaagc acatgttccc     60
ggcatgccgg ttatcgccgt tattggtgat ggccagctag ctcgcatgat gcaaaccgcc    120
gccattgagc tcggccaatc gctgcgcctt cttgccggcg cacgcgatgc ctctgcggca    180
caagtatgcg cggatgtagt gcttggtgat tacaccaact acgacgactt gctcaaagcc    240
gtcgacggtg ccaccgctgt cacttttgac catgagcacg tgcctaatga gcacctcacc    300
gcgttgatcg atgcaggcta taacgtgcag ccacaacctg ctgcgctgat taacgcccaa    360
gacaaattgg ttatgcgcga gcgcctcgcc gagctgggcg cacccgtgcc gcgctttgcg    420
ccgattgaat ctgcccaaga tgcgtacgat ttttggacct tgacgtccgg gcaggtctgt    480
ctgaaggcgc gccggggtgg ctacgacggc aaaggcgtgt ggtttccgaa taatgaatct    540
gagctgactg ctttggtctc tgacctttcg cgccgcggcg tggccttgat ggctgaagag    600
aaggttgcgc tggtccgcga gctttccgtg ctggtcgcgc ggactccctc gggcgaggtt    660
gctacttggc cgctgactga gtctgtgcag cgcaacggtg tgtgcgctga agctgtcgcg    720
ccagccccgg gagttgaccc gcagctgcag caacgcgctg agacactggg tgaaaagatt    780
gccaccgagt gggtgtaac tggtgtgctc gcggtagagc ttttgcatt tgcgaatgag     840 tccggtgcgg aagatatcgc ggttaatgaa ctggcaatgc gcccgcacaa taccggccac    900
tggaccctag atggttctgt gacctcccaa tttgagcagc acctgcgcgc ggtgatggat    960
gagccactgg gggatacatc cacgcttgcc ccagtcaccg tgatggccaa cgtcttaggc   1020
gctgacgaag acccaaagat gccaatgggc gagcgtgccc gagaagtggc gcgccgcttc   1080
ccgcgagcca agtccatct ctacggcaag gggcatcgcc caggccgtaa gattggccac   1140
gtgaacctca ccggtgagga cgtagaggca acccgtcgcg atgctcgctt ggctgcggat   1200
ttcctcgtga acgccgcgtg gtctgataac tggtccgcta aatagcaaga tgtatcaaga   1260
tatataagga aagaaatgac tgcaccgcta gttgggctca tcatgggctc tgattctgat   1320
tggccaaccg ttgaaccagc agctgaggtt ctcgccgaat tcggtgttcc ttttgaggtg   1380
```

| | |
|---|---|
| ggcgtggtct ctgcgcaccg cacgccggaa aagatgctgg attacgccaa gcaagcccac | 1440 |
| actcgcggca tcaaggtgat tgttgcttgt gccggtgggg cagcgcacct accaggcatg | 1500 |
| gtggctgcag caactccttt gccagttatt ggtattccac gtgccttgaa agatttggaa | 1560 |
| ggtctggact ctttgctgtc tatcgtgcag atgccagctg gggttccggt tgcgaccgtg | 1620 |
| tctatcggcg gcgctaagaa tgctggcttg ctcgccatcc gtaccctggg cgtgcagtac | 1680 |
| tcagaattgg ttgaacgcat ggccgattac caagaaaata tggccaagga agttgagcaa | 1740 |
| aaagacgcca atcttcgcgc caagctcatg ggggactag | 1779 |

<210> SEQ ID NO 41
<211> LENGTH: 888
<212> TYPE: DNA
<213> ORGANISM: Corynebacterium ammoniagenes
<220> FEATURE:
<221> NAME/KEY: gene
<222> LOCATION: (1)..(888)
<223> OTHER INFORMATION: purC

<400> SEQUENCE: 41

| | |
|---|---|
| atgcgcccac agctttctga ttatcagcac gtatcctccg gcaaagtccg cgatatctac | 60 |
| gaagtagatg acaacacttt gctcatggtg gtcaccgacc gcatctccgc ctatgacttc | 120 |
| gcactagagc cagccatccc cgataaaggc cgggttctta ccgcaaccac catgttcttc | 180 |
| ttcgacgcca tcgatttccc gaaccatttg caggaccca tcgatgatgc gcggattcca | 240 |
| gaagaagtat tgggccgagc gatcatcgtt aagaagctca acatgctgcc ctttgagtgc | 300 |
| gttgcccgcg gttacctcac cggttccggc ttgaaggaat acaacgctaa cggcaccgtg | 360 |
| tgcggcatcg agctgccaga aggcttggtt gaggcgtcgc gtctgccaga gccaattttc | 420 |
| accccagcca ccaaggcaga gcagggcgac acgatgaaaa acgtcagctt cgagcgcgtg | 480 |
| gtgcaggacc ttggccaaga gcgcgcagag cagcttcgcg atgaaaccct gcgcatctac | 540 |
| tccgccgccg ccaagattgc cgaagaaaag gcatcatct ggctgataca gaagtttgaa | 600 |
| ttcggccttg attccgaagg caatctggtc ttgggcgatg aagtacttac gcctgattcc | 660 |
| tcccggtact ggccagcaga cacctacgcg gaaggcattg tgcagcccag ctttgacaag | 720 |
| cagtacgtgc gcaactggtt gacctcggag gaatccggct gggatgtgga gtcggaaacc | 780 |
| cagccgccag tgcttcccga tgacatcgtc gccgccaccc gctgcgcta catcgaggct | 840 |
| tatgagcgct tgtccggcaa gcgtttcatc gacttcattg gcggttaa | 888 |

<210> SEQ ID NO 42
<211> LENGTH: 1551
<212> TYPE: DNA
<213> ORGANISM: Corynebacterium ammoniagenes
<220> FEATURE:
<221> NAME/KEY: gene
<222> LOCATION: (1)..(1551)
<223> OTHER INFORMATION: purH

<400> SEQUENCE: 42

| | |
|---|---|
| atgagtgatg accgcaagca gatcaagcgt gcactaatta gcgtttatga caagacaggg | 60 |
| ctcgaagagc tcgctcgcac gcttgacagc gcaggcgtag agattgtgtc caccggctcc | 120 |
| accgccgcca agattgctga tcttggtatt aacgtcactc cggttgaatc tctcaccgga | 180 |
| ttcccagagt gcctcgaagg ccgcgttaag accttgcacc cacgcgtgca tgcgggcatt | 240 |
| ttggctgata cccgcaagcc ggatcacctt aatcagctgg aagagcttga gattgagcca | 300 |
| ttccagttgg tcgtggttaa cctgtaccca tttaaagaga ctgtagcttc tggcgcagac | 360 |

```
ttcgatggtt gcgtcgagca gattgatatc ggcggtccat ccatggtccg tgctgctgcc    420
aagaaccacc catcggtggc ggttgttgta gacccagcgc gttacggcga catcgctgag    480
gctgtcgctc agggcggatt cgatctggcg cagcgtcgtc agctggccgc gactgcgttt    540
aagcacacgg cagattatga tgttgcagtt tctggctggt ttgcccagca gcttgccgat    600
gactctgttg cctctgctga gcttgaaggc gacgcgctgc gttatggtga aaccctcac     660 cagcaggctt ccatcgttcg tgaaggcacg accggtgttg ctaatgcgaa gcagctgcac    720
ggtaaggaaa tgagctacaa caactaccag gacgcggatg ccgcatggcg cgcggcttgg    780
gatcatgaac gtccatgtgt agcaattatt aagcacgcta acccttgcgg tatcgctgtt    840
tctgatgagt ccatcgcagc agcacacgca gcggcacacg cctgtgaccc aatgtccgct    900
ttcggtggcg ttattgcggt caaccgcgaa gtcaccaagg aaatggcaac ccaggttgct    960
gacatcttca ccgaggtcat catcgcaccg tcctacgaag atggagccgt cgagattttg   1020
cagggcaaga gaatattcg catccttgtt gctgagcatg aagtaccagc agtagaggtc   1080
aaagaaatct ctggtggccg tctgctgcag gaagcagacg tttaccaggc tgagggcgat   1140
aaggcttcga gttggacttt ggctgccggc gaagctgcat ccgaggaaaa gctcgcggag   1200
ctggaattcg cttggcgcgc agtacgctcg gtaaagtcca acgccatctt gttggcgcat   1260
gaaggtgcaa ccgttggcgt gggtatgggc caggtcaacc gcgttgattc ggcgaagttg   1320
gctgttgacc gcgcgaatac tttggctgat tccgcagagc gtgctcgcgg ttccgtcgca   1380
gcatcggatg cgttcttccc attcgccgat ggcttgcagg tgcttatcga tgccggcgtt   1440
tccgccgttg tccagcccgg cggctccatc cgcgatgaag aagttattgc tgccgctgaa   1500
gcagccggta tcaccatgta cttcactggc acccgccact tcgcgcacta a            1551

<210> SEQ ID NO 43
<211> LENGTH: 1020
<212> TYPE: DNA
<213> ORGANISM: Corynebacterium ammoniagenes

<400> SEQUENCE: 43
atgaccggca agatttctga tagccgcaag aatatgatgc tgttttccgg gcgcgcccac     60
ccagagttgg gtgaggctgt tgccaaggaa ttgggcactg acttggttcc taccaccgcc    120
cgtgactttg cgaatggcga aatcttcatt cgcttcgaag agtccgttcg tggtgcagat    180
tgctttgttt tgcagtccca cacccagccg ttgaacaagt ggctcatgga gcagctcatc    240
atgattgatg cgctcaagcg tggttccgct aagcgcatca cggccatctt gccgttctac    300
ccatatgctc gccaggacaa gaagcacctc ggtcgcgagc ctatttccgc tcgcctagtg    360
gctgacctgc tggctaccgc aggtgctgac cgcattgtgt cggtggactt gcacaccgac    420
cagatccagg gtttcttcga cggccctgtc gatcacatgc acgccatgcc gattttgacc    480
gagtacatcc agtccaagta ctccatcgac aacattgttg tggtctcccc agatgcaggc    540
cgcgtcaagg ttgcagaaaa gtgggcgcat gagcttggcg atgccccact ggcattcgtt    600
cacaagtctc gctccaacac tgaagcgaat aaaaccgtgt ccaaccgcgt ggtcggtgat    660
attgagggca aggactgcat cttgctcgat gacatgattg ataccggcgg caccatcgct    720
ggcgcggtcc gcgtactgcg tgaagctggc gcacgttccg tcgttatcgc atgtacccac    780
ggcgttttct ctgaccccgc acgcgagcgt ctgtctgagt gcggtgctga ggaagttatc    840
accaccgaca ccttgcctca gtccaccgag ggctgggaca acctcaccgt gctgtcgatc    900
```

```
gcgccgctgt tggcacgtac gattcatgag atcttcgaaa atggttcggt aaccaccctc    960
ttcgagtccg cgtagaaaaa tctgagagat ttttctacag gataagacca aataggaccg   1020
```